(12) United States Patent
Baillet et al.

(10) Patent No.: US 7,755,762 B2
(45) Date of Patent: Jul. 13, 2010

(54) METHOD OF IMPROVING A COLOR FILTER

(75) Inventors: Gilles Baillet, Charenton le Pont (FR); Bernard Bourdoncle, Charenton le Pont (FR); Margalith Harrar, Charenton le Pont (FR); Françoise Vienot, Paris (FR)

(73) Assignees: Essilor International (Compagnie Generale d'Optique), Charenton le Pont (FR); Centre National de la Recherche Scientifique-CNRS, Paris (FR)

( * ) Notice: Subject to any disclaimer, the term of this patent is extended or adjusted under 35 U.S.C. 154(b) by 527 days.

(21) Appl. No.: 11/839,072

(22) Filed: Aug. 15, 2007

(65) Prior Publication Data

US 2008/0055599 A1  Mar. 6, 2008

(30) Foreign Application Priority Data

Aug. 16, 2006  (FR) .................................. 06 07324

(51) Int. Cl.
*G01N 21/25* (2006.01)
(52) U.S. Cl. ...................................... 356/407; 356/408
(58) Field of Classification Search ......... 356/406–408, 356/230, 124, 124.5, 418–421, 425; 362/2, 362/293; 250/226

See application file for complete search history.

(56) References Cited

U.S. PATENT DOCUMENTS 7,659,982 B2 * 2/2010 Baillet et al. ................. 356/406

* cited by examiner

*Primary Examiner*—Gregory J Toatley, Jr.
*Assistant Examiner*—Tri T Ton
(74) *Attorney, Agent, or Firm*—Occhiuti Rohlicek & Tsao LLP

(57) ABSTRACT

A method of improving an initial color filter comprises a numerical generation of sinusoidal spectra. Two steps of selecting said spectra are then executed. The first selection is carried out according to a criterion of colorimetric similitude with respect to the initial filter. The second selection is carried out according to the capacity of dummy filters corresponding to each spectrum to restore hues in a natural manner. To do this, observations of samples of hues through each dummy filter are simulated numerically, using a color appearance model to take account of a visual perception of a human observer. In this way, an improved filter is determined, which has a color close to that of the initial filter and which affords a natural rendition of hues.

13 Claims, 6 Drawing Sheets

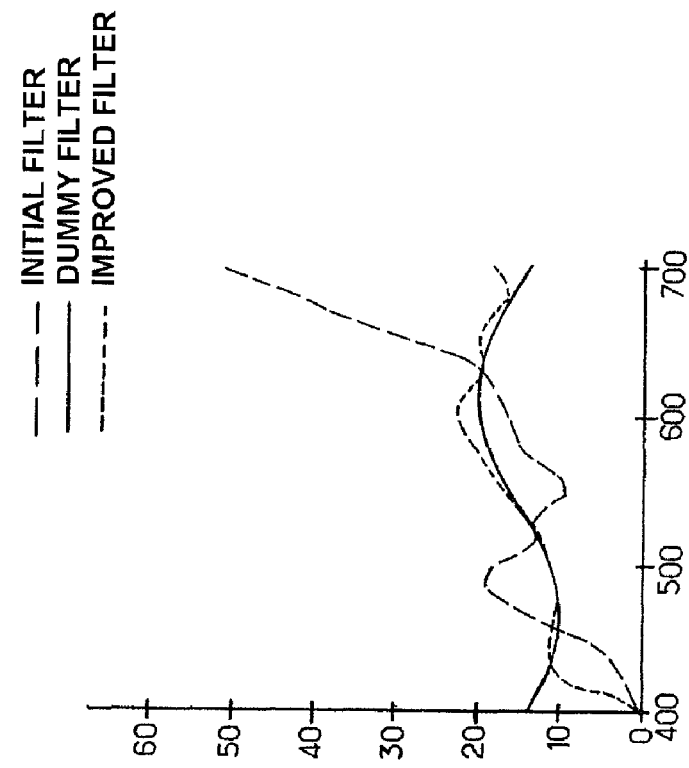
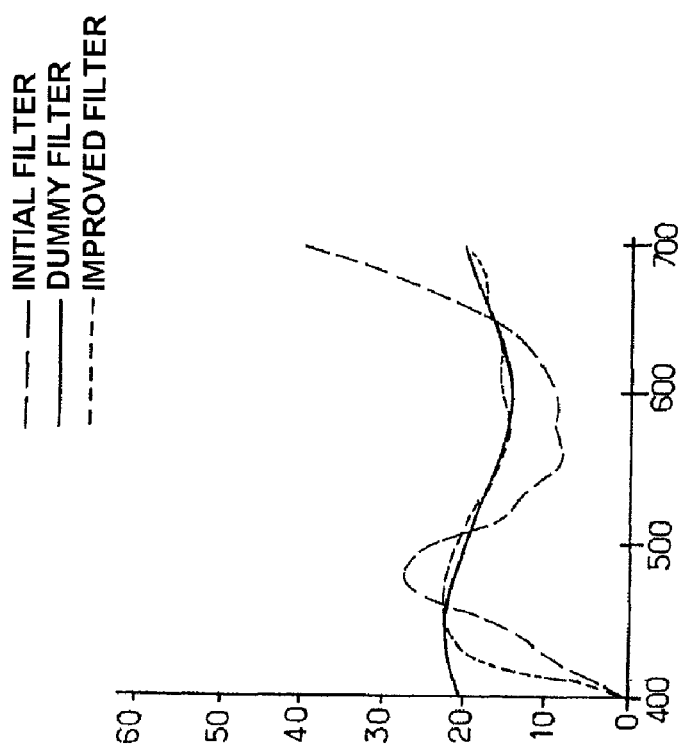

METHOD OF IMPROVING A COLOR FILTER

CROSS-REFERENCE TO RELATED APPLICATIONS

This application claims the benefit of French Application No. 06 07324, filed Aug. 16, 2006, the content of which is hereby incorporated by reference in its entirety.

FIELD OF DISCLOSURE

The present invention relates to a method of improving a color filter. It may be applied, in particular, to improve a tinted ophthalmic lens.

BACKGROUND

Color filters are used in numerous applications, for example to attenuate an overly large luminous intensity or to increase an image contrast. In particular, tinted ophthalmic lenses, especially solar protection lenses, are color filters which are intended to be fitted into a spectacle frame.

Theoretically, a filter can exhibit a transmission spectrum which is substantially flat in the visible light interval 380 nm-780 nm (nanometer). However, such a filter with flat spectrum cannot be achieved in practice, especially on account of spectral limitations of the dyes which are used to manufacture filters. Moreover, the grey appearance of a flat-spectrum filter would be rather unaesthetic and rather unappealing for ophthalmic applications. The spectrum of a real filter therefore exhibits variations in the visible light interval. The filter is then liable to modify the perception of hues by an observer, between a direct observation of samples of these hues and an observation of them through the filter. For this reason, a real filter is called a color filter.

The improving of a color filter is generally a lengthy and difficult task. Specifically, not only must the hue of the filter be adjusted as a function of aesthetic or marketing criteria, but the filter must not overly much alter the hues of objects which are observed through it. Stated otherwise, a natural rendition of hues by the filter is sought. In order to propose an improvement of an initial color filter, it is then necessary to manufacture a range of color filters which correspond to as many modifications made to the initial filter, and to compare the modified filters with one another and with the initial filter as regards the restitution of hues by the filters. Such a mode of operation is lengthy and expensive, especially because a set of observers must be summoned to compare the filters. Furthermore, the filter evaluations which are produced by the observers are prone to variations, on account of their subjective nature. It is then necessary to repeat the evaluations performed by the observers, in order to subsequently calculate an average of the results obtained.

To alleviate these difficulties, document EP 1,273,894 proposes a method of obtaining a range of color filters, which is based on calculating chromatic deviations expressed in the CIELAB space, defined by the Commission Internationale de l'Eclairage. The involvement of observers is then no longer necessary for visually evaluating samples of hues seen through each filter. Nevertheless, the method which is described in this document is based on the initial manufacture of real test filters, this being lengthy and complex and in practice limits the evaluations to easily achievable filters. Furthermore, the chromatic deviations calculated give a poor account of the impression, for a human observer, of a rendition of hues which is natural.

An object of the present invention is to propose a method of improving a filter, which does not have the preceding drawbacks.

SUMMARY

To this end, the invention proposes a method which comprises the following steps:

/1/ determining colorimetric coordinates of an initial color filter;

/2/ numerically generating a first set of transmission spectra having respective variations which consist of sinusoids over a visible light interval;

/3/ for each spectrum of the first set, calculating colorimetric coordinates of the spectrum;

/4/ within the first set of numerically generated spectra, selecting a second set of spectra the colorimetric coordinates of which correspond substantially to those of the initial filter;

/5/ for each spectrum of the second set, quantitatively evaluating a dummy filter corresponding to this spectrum, a result of this evaluation characterizing a capacity of this dummy filter to restore at least one hue and being obtained by using a numerical model of color appearance to simulate a visual perception of a sample of this hue through the dummy filter; and /6/ within the second set of spectra, selecting the one which exhibits the best quantitative evaluation to constitute an improvement of the initial filter.

A color filter can then be manufactured, which exhibits a transmission spectrum which is substantially equal to the spectrum selected in step /6/.

Such a method of improving a color filter is economical and fast to implement, in particular because it does not necessitate any recourse to observers. It merely requires calculation means, and optionally spectrophotometric measurement means, which are simple and commonly available.

Furthermore, such a method makes it possible to propose improvements of the initial filter which would not appear by making real color filters derived from the initial filter. Indeed, filter manufacturing constraints, in particular spectral limitations of the dyes which are used to make the filters, may prevent the possibility of filters which correspond to spectra having industrial or commercial interest. A method according to the invention, because it undertakes numerical simulation of dummy filters, allows the identification of possibilities for improving an initial filter which would not be accessible with real test filters.

A method according to the invention undertakes two successive selections. The first selection is based on the colorimetric coordinates of filters which would correspond to the numerically generated spectra. These colorimetric coordinates, which are used in steps /1/, /3/ and /4/, may be the coordinates L*, a*, b* of the CIELAB space defined by the Commission Internationale de l'Eclairage (CIE).

The second selection is based on evaluating the restitution of at least one hue by each dummy filter. In this way, the improved filter which is determined on completion of the method satisfies both a requirement regarding apparent color of the filter and a requirement regarding restitution of hues.

Stated otherwise, the invention makes it possible to identify a filter spectrum which corresponds to initial values of colorimetric coordinates, while seeking improved restitution of hues.

The use of spectra, at least certain of which have variations which consist of sinusoids, is particularly advantageous. Specifically, a large number of such spectra may be easily generated numerically, by varying at least one sinusoid parameter chosen from a period, an initial phase, an amplitude and a base constant added to the sinusoids. A spectrum which is generated numerically in step /2/ may consist of a single sinusoid, optionally added to a base constant. Alternatively, it may consist of a linear combination of several sinusoids, which may also be added to a base constant.

An important characteristic of the invention is the use, in step /5/, of a numerical model of color appearance. Such a model makes it possible to take account of physiological and subjective phenomena which are involved in the visual perception of hues by a human being. Variations in the sensitivity of the human eye as a function of the hue itself or of other environmental parameters are thus taken into account, along with differences in assessment of hues which may result from psychological factors. The quantitative evaluation which is carried out in step /5/, to characterize the restitution of the hue of the sample by a dummy filter, consequently corresponds to a real evaluation, such as it would be performed by a human observer with a real sample of the filter.

According to a preferred mode of implementation of the invention, the numerical color appearance model, which is used in step /5/, may be the CIECAM02 model ("Color Appearance Model for Color Management Systems") defined in 2002 by the Commission Internationale de l'Eclairage in publications ISBN 3 901 906 290 and CIE 159: 2004. The inventors have verified that the evaluations of color filters which are performed using this model correspond in satisfactory measure to evaluations performed by a set of human observers.

Step /5/ of a method according to the invention may itself comprise the following substeps, which are performed for each numerically generated spectrum of the second set:

/5-1/ obtaining, on the basis of the numerically generated spectrum and of a reflection spectrum of the hue sample, optical data relating to a simulation of an observation of this sample through a dummy filter corresponding to the numerically generated spectrum;

/5-2/ introducing, into the numerical model of color appearance, the optical data relating to the simulation of the observation of the hue sample through the dummy filter corresponding to the numerically generated spectrum, so as to obtain, for said sample, a value of at least one visual perceptive attribute; and /5-3/ calculating a deviation between the perceptive attribute value obtained for the simulation of the observation of the hue sample through the dummy filter which corresponds to the numerically generated spectrum and a value of said perceptive attribute for an observation of the same sample without the filter, The deviation which is calculated in step /5-3/, between the perceptive attribute value which is obtained for the hue sample by simulating an observation of the latter through the dummy filter and the value for an observation without the filter, constitutes an evaluation of the restitution of the hue of the sample by the dummy filter. Stated otherwise, this result of the evaluation characterizes the capacity of the filter to restore the hue in a natural manner, that is to say the impression of an observer to perceive the real hue through the filter.

The optical data which are obtained in step /5-1/ may be trichromatic components relating to the simulation of the observation of each hue sample through the dummy filter whose evaluation is in progress.

The visual perceptive attribute value which is obtained in step /5-2/ may be a value of hue angle H which may be read off from the NCS system ("Natural Color System") known to a person skilled in the art.

According to a refinement of the invention, steps /5-1/ to /5-3/ may be repeated for several samples of hues, so as to obtain respective deviations of perceptive attribute for these, samples of hues. The method then comprises the following additional step:

/5-4/ calculating a value characterizing the global restitution of the hues by the dummy filter, on the basis of the set of deviations of perceptive attribute that are obtained respectively for the samples of hues used.

The evaluation which is thus obtained of the restitution of hues by the dummy filter is based on several hues. It makes it possible to evaluate the filter in a global manner while taking account of conditions of use which are varied, that is to say for a multiplicity of hues which would be perceived through the filter. The value which characterizes the global restitution of the hues by the filter may then be used for the selection of step /6/.

The invention also proposes the use of an improving method as described previously to improve a tinted ophthalmic lens. In this case, the refinement of the method which consists in using several samples of hues to carry out an evaluation of the global restitution of hues by dummy ophthalmic lenses is particularly advantageous. Specifically, an ophthalmic lens may be used by a wearer of the latter under highly varied conditions, which depend on his luminous environment as well as on the objects that the is observing.

Other features and advantages of the present invention will appear in the description hereinbelow of a nonlimiting exemplary implementation, with reference to the appended drawings, in which:

DESCRIPTION OF THE DRAWINGS

FIGS. 6a and 6b are spectral diagrams illustrating the respective improvements of the grey and brown filters considered for FIGS. 5a and 5b.

DETAILED DESCRIPTION

Figure 1:
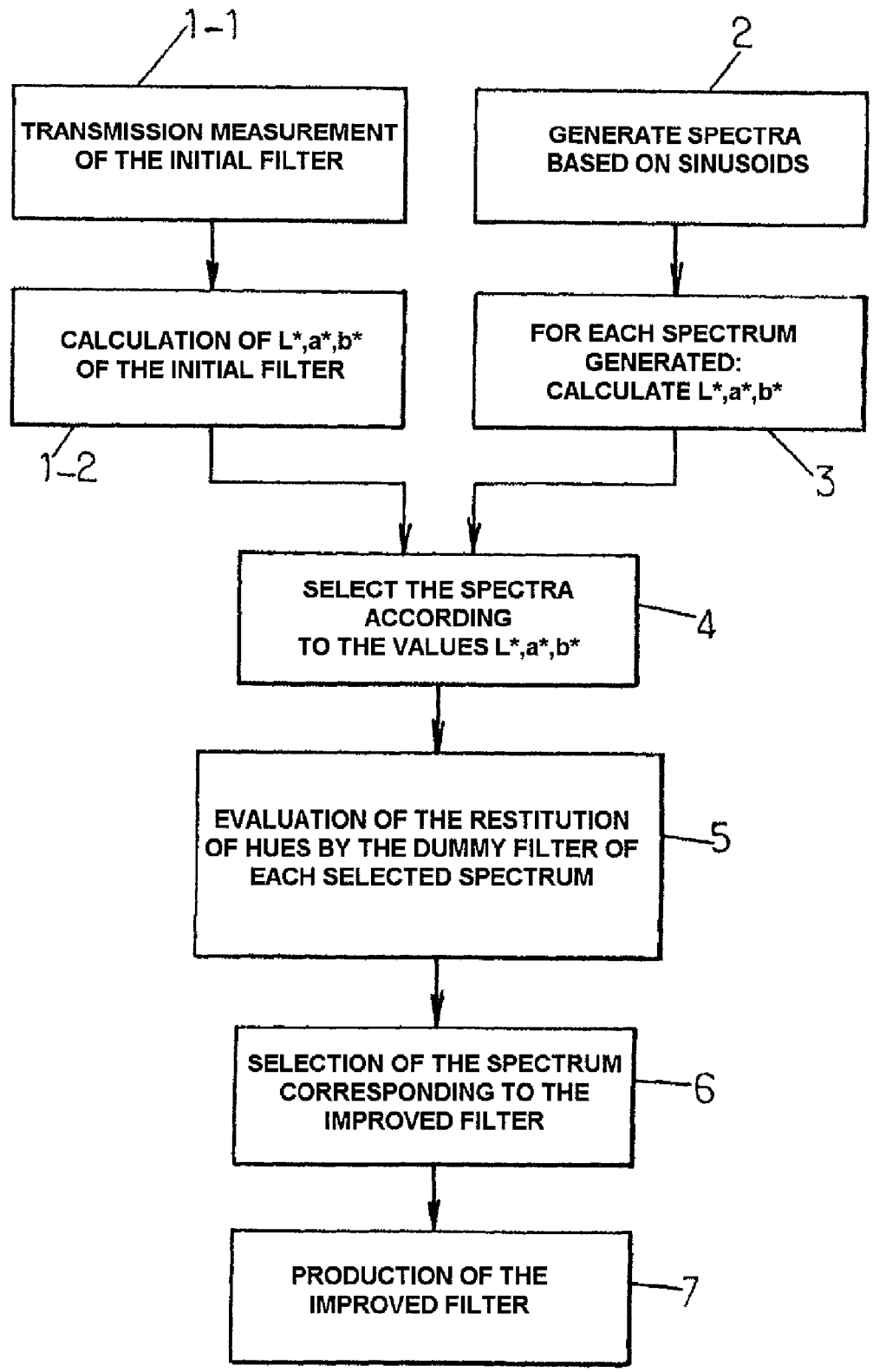
FIG. 1 is a schematic diagram of the steps of a method according to the invention, for improving an initial color filter.

The improvement of a color filter in accordance with the invention is now described, with reference to FIG. 1.

During a first step reference 1-1, an initial color filter is characterized in transmission with the aid of a spectrophotometer, which may be of a standard commercially available type. A transmission spectrum of the filter is thus obtained, which groups together transmission values measured for wavelengths distributed within a visible light interval. For example, the transmission of the filter may be measured over the wavelength interval 400 nm -700 nm with a spacing of 1 nm.

Colorimetric coordinates of the initial filter are then calculated from the measured transmission spectrum (step 1-2). In the mode of implementation of the invention which is described here, these coordinates are L*, a*, b* of the CIELAB space. The mode of calculating these coordinates is assumed to be known and is not repeated here. The coordinates L*, a*, b* calculated for the initial color filter are intended to constitute target values for a first step of selecting spectra, which will be set forth later.

Figure 2:
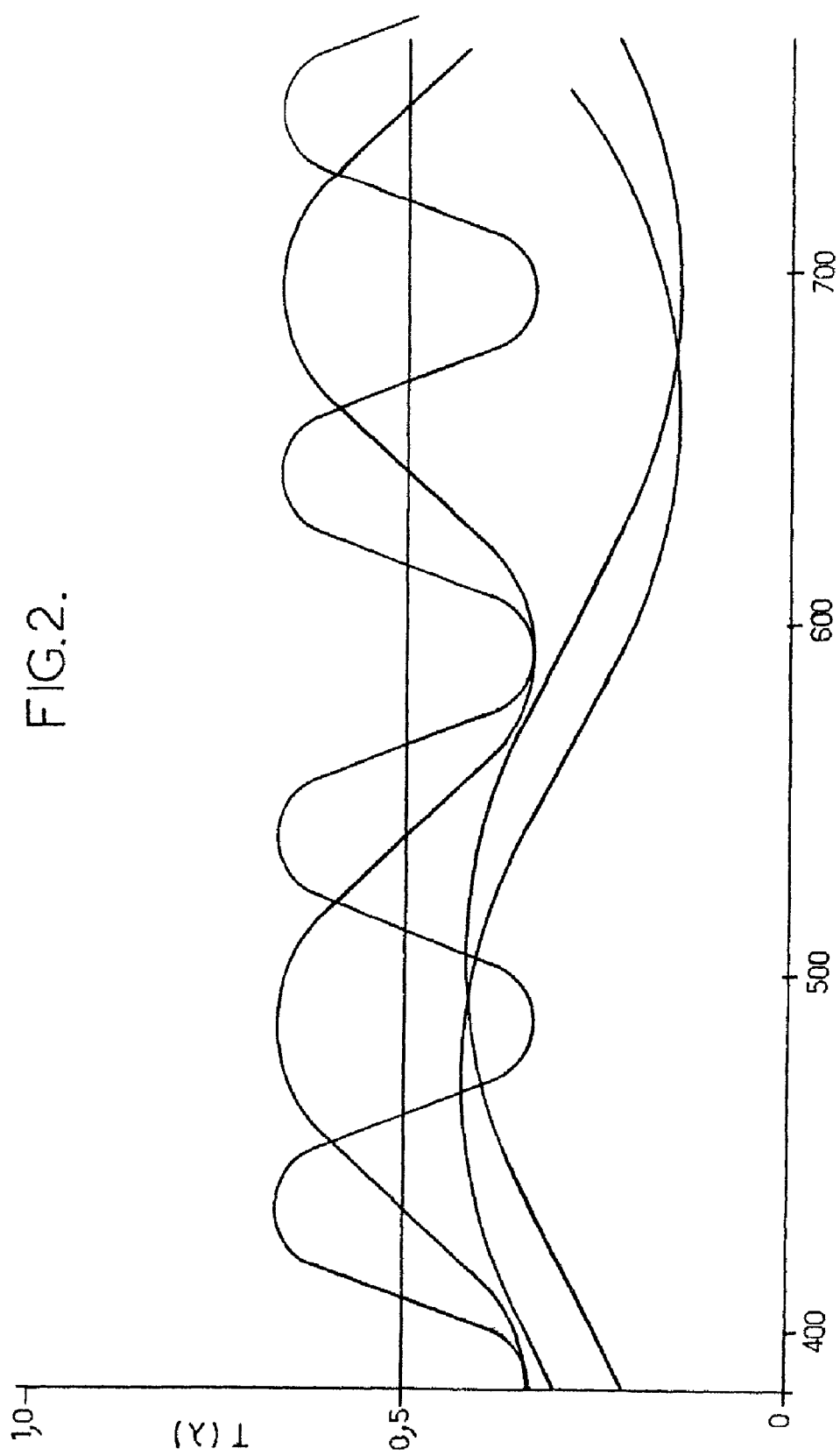
FIG. 2 is a diagram representing transmission spectra of numerically generated filters.

During step 2, a first set of spectra is generated numerically. These spectra, which characterize dummy color filters, are defined over the visible light wavelength interval 400 nm -700 nm, for example also with a spacing of 1 nm. The inventors have discovered that these spectra can be constructed from sinusoidal functions over the 400 nm -700 nm interval, without such a restriction resulting in a limitation of the space of the spectra taken into account which could prevent the identification of possibilities for improving the initial filter. These spectra may be generated from a first sinusoidal function by varying parameters of the latter, such as its frequency, its initial phase, its amplitude or a base constant which is added to the sinusoidal function. These variable parameters appear more clearly in the following expression for the transmission of a dummy filter:

$$T(\lambda)=B+A\times\sin(2\pi\alpha\times\lambda+\beta)$$

where $\lambda$ denotes a wavelength in the 400 nm -700 nm interval, T is the transmission of the dummy filter, A is the amplitude of the sinusoidal function, B is a base constant, $\alpha$ and $\beta$ are respectively the frequency and the original phase of the sinusoidal function. Validation of the limiting of the space of the numerically generated spectra to a set of sinusoidal spectra results from the finding that the colorimetric coordinates of any spectrum are usually quite close to those of the principal component of the decomposition of this spectrum into a Fourier series. FIG. 2 is a spectral diagram which reproduces the variations of such numerically generated spectra. In this diagram, the oscillation period of the spectra varies between the length of the visible light interval 400 nm -700 nm and a quarter of this length.

The numerically generated spectra may also each be of the form of an average of several sinusoidal functions of the above type. The transmission of the dummy filter may then be expressed in the following manner:

$$T(\lambda)=B+[\Sigma_{i=1 \, to \, n}\{A_i\times\sin(2\pi\alpha_i\times\lambda+\beta_i)\}]/i$$

where $A_i$, $\alpha_i$ and $\beta_i$ correspond to the above parameters A, $\alpha$ and $\beta$ for each sinusoidal function which is combined and read off from the index i. n denotes the number of sinusoidal functions which are combined in the spectrum. On account of the proliferation of parameters which are then required to define each spectrum, it may be useful to employ a criterion to initially limit the number of spectra of this form which are generated. Such a criterion will be stated later, in conjunction with the formulating of diagrams of perceptive attribute deviations calculated for a series of hue samples. The use of the average of the sinusoids results from the finding that a transmission spectrum of a filter may be recomposed on the basis of the combination of the sinusoidals of a larger amplitude which is obtained when decomposing the spectra into a Fourier series. This recomposition is validated by the fact that the original spectrum is recombined from the sinusoids that restore the similar hues.

For each spectrum which is numerically generated, the corresponding coordinates L*, a*, b* are calculated (step 3), and the values obtained are compared with the target values which were calculated for the initial color filter (step 4). The numerically generated spectra for which the values of L*, a*, b* are close to the target values are then selected. Various automatic selection criteria may be used in an equivalent manner, to discriminate those of the numerically generated spectra which correspond to values of L*, a*, b* that differ too much from those of the initial filter. These criteria may pertain to a quadratic deviation calculated between the values of L*, a*, b* of the numerically generated spectrum and the target values, or to the largest of three absolute differences between the value of a coordinate for the numerically generated spectrum and the corresponding target value. Step 4 constitutes a first selection of the numerically generated spectra, on completion of which the selected spectra all exhibit a color close to that of the initial filter. For example, this color may be grey, green or brown, in particular when the method is applied to improve an ophthalmic lens for solar protection.

Figure 3:
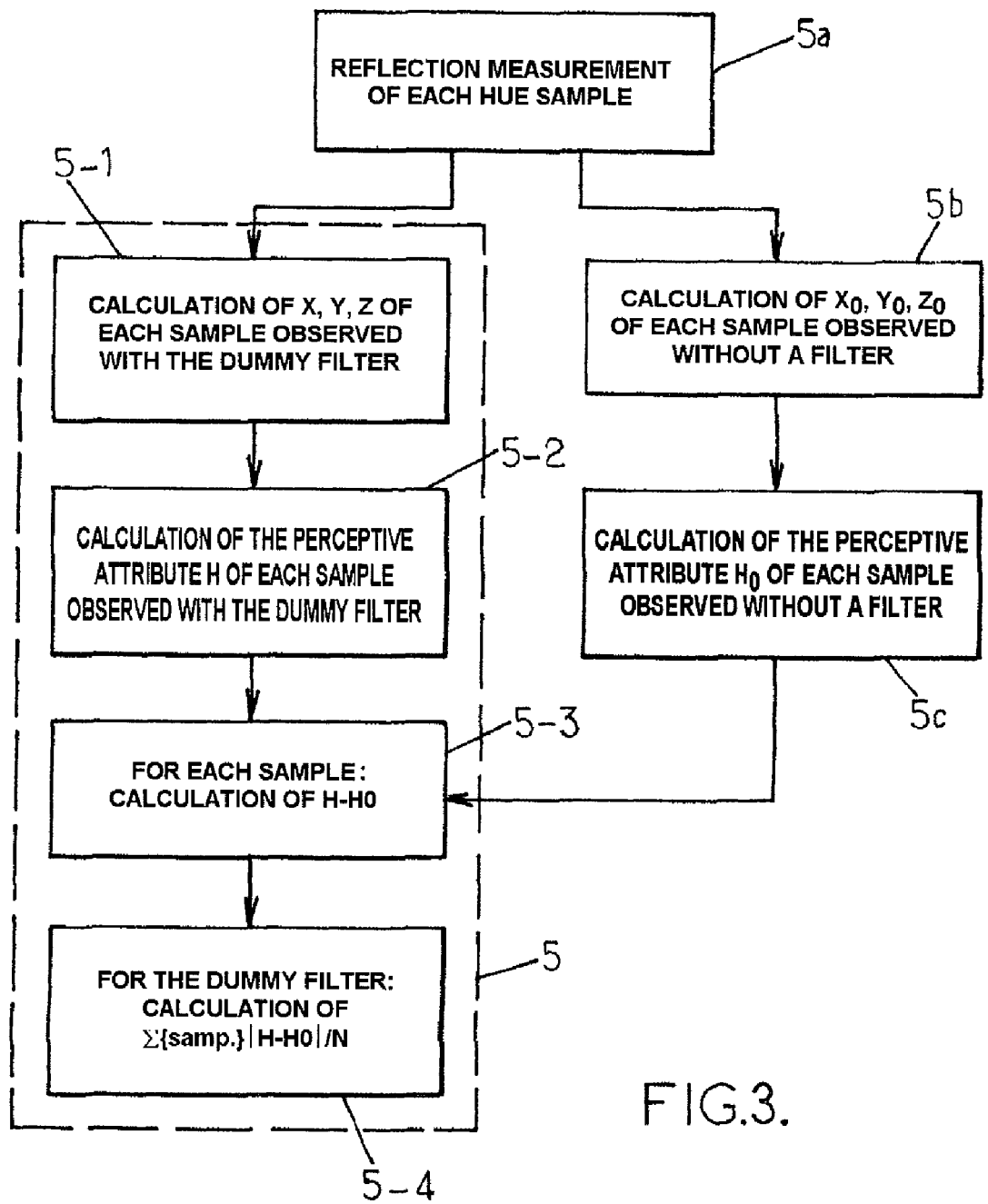
FIG. 3 is a schematic diagram detailing one of the steps of FIG. 1.

During step 5, the capacity of the dummy filter which corresponds to each of the spectra selected in step 4, to restore reference hues (FIG. 3) is evaluated.

Samples of these hues are constructed from opaque supports colored uniformly on one face. Standardized samples of hues may be used, such as those which are fixed by the NCS ("Natural Color System", see NCS Atlas 1950 Original) system. These latter are distributed in series of 40 samples, each series corresponding to a variation of the hue of the samples, and the series being differentiated from one another by values of saturation ("chromativeness") and brightness ("brightness" or again "1-blackness"). The samples of hues of one and the same series may be used to evaluate each dummy filter selected in step 4. Specifically, the inventors have shown that evaluations of any filter which are performed on the basis of different series of samples of NCS hues culminate in equivalent quantitative results, whereas these series are differentiated by the values of brightness and saturation of the hues. A reflection spectrum of each of the hue samples used is then obtained over the visible light wavelength interval 400 nm -700 nm, for example by spectrophotometric measurement (step 5a of FIG. 3). Preferably, the reflection spectrum of each hue sample is a nonspecular reflection spectrum, which corresponds better to real observation conditions, with respect to a specular reflection spectrum. Stated otherwise, the reflection spectra of the samples of hues correspond to values of angles of incidence and reflection of light which are different from those defined by the Bragg reflection conditions.

For each hue sample and for each spectrum selected in step 4, the spectral reflection values of the sample are combined with those of the selected spectrum and with spectral characteristics of an illuminating light source (step 5-1). Optical data are thus obtained, which characterize the hue sample when it is illuminated by the light source and observed simultaneously through the dummy filter which corresponds to the selected spectrum. In particular, the spectral characteristics which are used for the light source, also called the illuminant, may correspond to the "SoLux® Daylight" illumination conditions, a light source as described in U.S. Pat. No. 5,418,419. In the mode of implementation of the invention which is described here, the optical data which are obtained are the trichromatic components X, Y, Z relating to the simulation of the observation of the hue sample through the dummy filter.

The X, Y, Z components are calculated in a manner which is known, using simple calculation means such as a personal computer. It is understood that in alternative modes of implementation of the invention, other optical data may be used in an equivalent manner.

During step 5-2, the X, Y, Z components which correspond to the simulation of the observation of each hue sample through each dummy filter are introduced into a color appearance numerical model. The inventors have validated experimentally that the CIECAM02 numerical model corresponds in a satisfactory manner to an average human visual perception. For this reason, the use of this model is preferred by the inventors. This numerical model, which may be implemented on a standard personal computer, produces values of visual perceptive attributes which characterize the perception of each hue introduced as input through its optical data. It takes into account, during simulation of the perception of each hue, of the real observation conditions. In particular, it is considered that the hue sample is observed inside a light booth with white and diffusing walls. In the mode of implementation of the invention which is described here, the perceptive attribute value which is used is that of the hue angle H which may be read off from the NCS system. It varies according to a circle between 0° and 360°, the values 0°, 90°, 180° and 270° corresponding respectively to the colors red, yellow, green and blue, and the hue varying continuously between these colors for intermediate values of H. The hue angle H is therefore particularly appropriate for distinguishing the samples within the NCS series used.

In parallel, optical data relating to each hue sample are calculated, which correspond to this sample when it is observed directly, that is to say considering there to be no interposed dummy filter, and using the same illuminating light source as previously. Trichromatic components $X_0$, $Y_0$, $Z_0$ are thus calculated for each hue sample used (step 5b). They are then introduced into the CIECAM02 model to obtain a value $H_0$ of a hue angle which characterizes the visual perception of the sample observed without a filter (step 5c). Given that steps 5a, 5b and 5c relate to the samples of hues independently of the dummy filter spectrum which is currently being evaluated, they are executed once only. The values which are obtained for the hue samples observed without a filter are then re-used to successively evaluate all the dummy filters which correspond to the spectra selected in step 4.

Figure 4A:
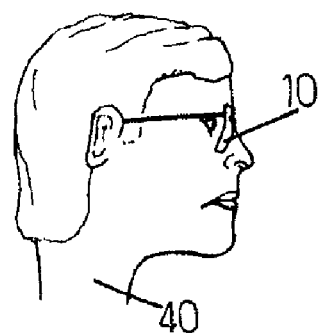
FIGS. 4a and 4b illustrate the observation conditions which are considered when evaluating a filter.
Figure 4A:
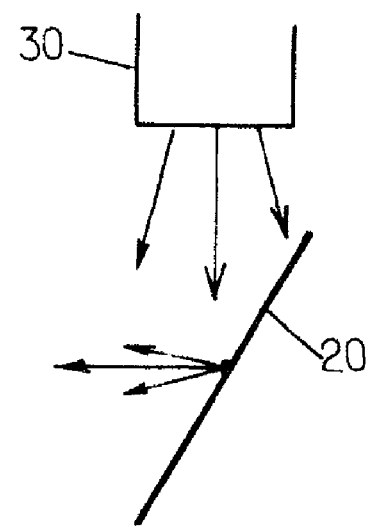
Figure 4B:
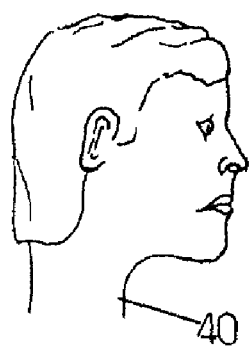
Figure 4B:
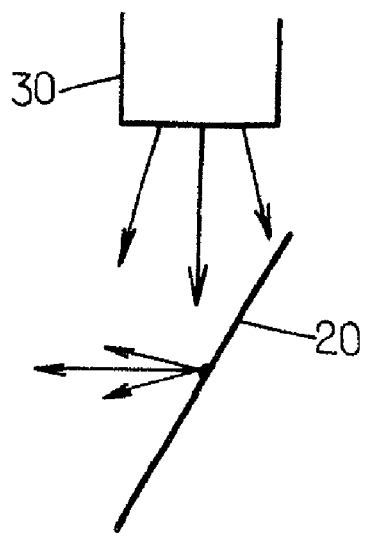

FIGS. 4a and 4b illustrate the observation conditions which correspond respectively to the values H and $H_0$ for each hue sample. The hue sample 20 is illuminated by the light source 30, which possesses an emission spectrum corresponding to the illuminant used for the calculation of the components X, Y, Z. The value H, such as it results from steps 5-1 and 5-2 for each dummy filter, corresponds to the case where the sample 20 is looked at by the observer 40 through the dummy filter 10, the filter 10 being disposed between the sample 20 and the eye of the observer 40. By way of illustration, FIG. 4a illustrates a case where the filter 10 is a tinted ophthalmic lens, in particular a lens of sunglasses. However, the filter 10 may also be, in an equivalent manner, a tinted helmet visor, a protective mask glass, a filter of an optical measuring or sighting apparatus, etc. FIG. 4b illustrates the observation conditions which correspond to the value $H_0$. They are identical to those of FIG. 4a, when dispensing with the filter 10.

Returning to FIG. 3, during step 5-3, a difference is calculated for each hue sample and for each dummy filter spectrum, between the hue angle value H which corresponds to this sample when it is observed through the dummy filter and the value $H_0$ which corresponds to the same sample observed without a filter. The absolute value of the difference $H-H_0$, denoted $|H-H_0|$, constitutes an evaluation of the restitution of the hue of the sample by the filter. A low value of $|H-H_0|$, typically less than 0.1, indicates that a color filter corresponding to the spectrum would hardly modify the perception of the hue of the sample, and a high value (greater than 0.1 in particular) indicates that it would cause an appreciable modification.

The global restitution of hues by each dummy filter may be evaluated by calculating an average of the absolute values of the perceptive attribute deviations obtained respectively for the hue samples and for this filter (step 5-4). Thus, the result of the evaluation of the dummy filter, denoted R, is equal to $\Sigma_{\{samples\}}|H-H_0|/N$, where N is the number of hue samples which were used to evaluate the filter. For example, N may be equal to 40 when a complete series of NCS hue samples has been used. Other equivalent formulae may be adopted alternatively for the evaluation result R.

Returning to FIG. 1, the dummy filter spectra selected in step 4 are ranked in ascending order to the results R. Those which appear first in this ranking correspond to a more natural restitution of hues, whereas those at the end of the ranking correspond to a larger alteration of the perception of hues. The spectrum which corresponds to the lowest result value R is then selected (step 6). The dummy filter which is associated with this spectrum constitutes an improvement of the initial color filter.

During step 7, a real color filter can be manufactured which corresponds to the spectrum selected in step 6. The mode of manufacturing such a filter is assumed to be known to a person skilled in the art and is not repeated here. In particular, dyes are selected and mixed in proportions appropriate to a transparent material intended to constitute a matrix of the filter. These proportions are determined as a function of the spectrum selected and of the absorption characteristics of the dyes, so as to obtain a real filter whose spectrum is as close as possible to the selected spectrum.

Figure 5B:
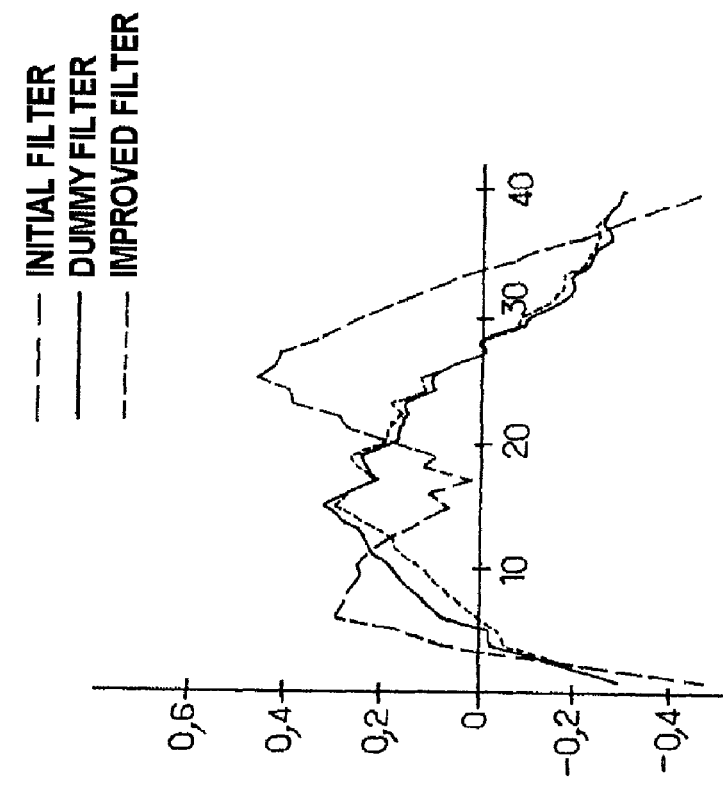
FIG. 5b corresponds to FIG. 5a for a brown initial filter.

FIGS. 5a, 6a and 5b, 6b illustrate improvements of filters which have been achieved according to the invention, for grey initial filters (FIGS. 5a and 6a) and brown initial filters (FIGS. 5b and 6b).

Figure 5A:
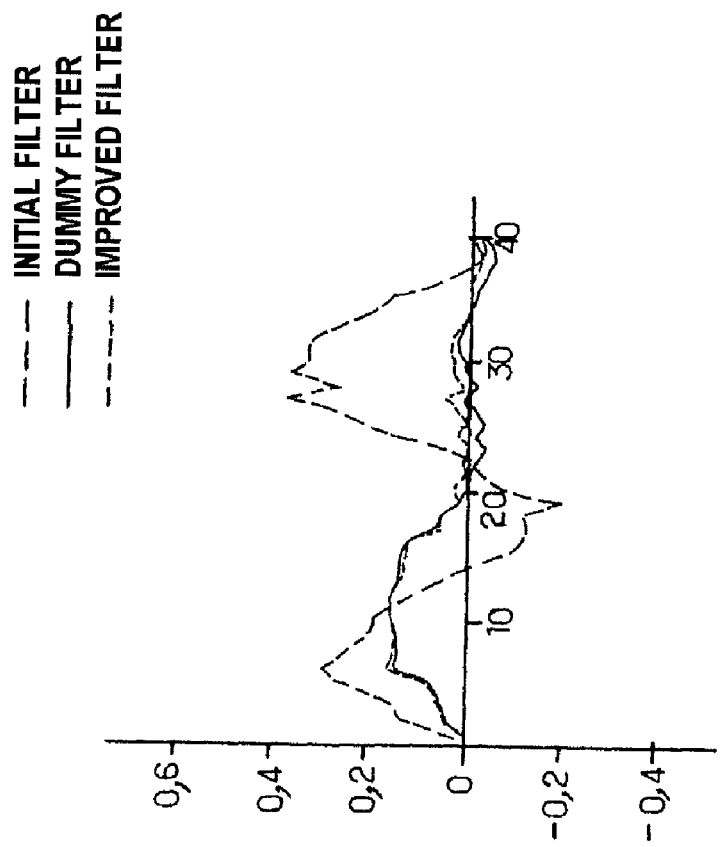
FIG. 5a is a comparison of three diagrams of perceptive attribute deviation values obtained for a grey initial filter and for a series of samples of reference hues, respectively for the initial filter, for a dummy filter selected according to the invention and for a manufactured filter which corresponds to the dummy filter selected.

FIG. 5a is a diagram which groups together, for the grey initial filter, for the dummy filter of the spectrum selected in step 6 and for the improved filter manufactured in step 7 which correspond thereto, the values of the difference $H-H_0$ which are obtained for the 40 samples of hues of the NCS series used. The hue samples are labelled as abscissa by a numbering of the latter in the NCS series, and the corresponding values of $H-H_0$ are labelled as ordinate. These values are obtained from transmission spectra measured for the initial filter and for the improved filter. Such a diagram provides a representation of the modification of the perception of hues which is caused by each filter. In this diagram, a curve close to the abscissa axis indicates that the filter affords a natural perception of hues, with a much reduced alteration of the latter. Parts of the curve which have positive ordinate values correspond to hues which are perceived in an offset manner when rotating clockwise around the NCS circle. Conversely, parts of the curve with negative ordinate values correspond to hues which are perceived in an offset manner when rotating in the trigonometric direction around the NCS circle. In the representation of FIG. 5a, the variations which correspond to the dummy filter selected and to the improved filter have lower amplitudes than those of the initial filter.

The values of R calculated for this first example are: 0.16 for the grey initial filter, 0.055 for the dummy filter selected in step 6 and 0.060 for the improved filter which was manufactured. These latter two are very close to one another, and are less than the value of R for the initial filter. This comparison quantifies the improvement which was obtained for the initial filter, in terms of restitution of hues.

FIG. 6a reproduces the spectrum of the grey initial filter considered in FIG. 5a, over the visible light wavelength interval 380 nm -780 nm, and also the spectrum selected in step 6 for this initial filter and the spectrum of the improved filter manufactured in step 7. These latter two exhibit variations which are similar, and which are less than those of the spectrum of the initial filter.

FIGS. 5b and 6b correspond respectively to FIGS. 5a and 6b, for a brown initial filter. The values of R calculated for this second example are: 0.23 for the brown initial filter, 0.171 for the dummy filter selected in step 6 and 0.174 for the improved filter which was manufactured.

When a method of improving a color filter as described previously has been implemented, on the basis of numerically generated spectra which each correspond to a single sinusoid, it is possible to further improve the filter by using spectra each formed from a combination of sinusoids. The inventors have discovered that the color restitution diagrams predicted by the color appearance numerical model, when they are combined linearly (average), give the same results as if the corresponding transmission spectra are combined and introduced into the model. On the basis of this finding, it is possible to examine the diagrams of the type of those of FIGS. 5a and 5b, which are obtained for the spectra each consisting of a single sinusoid. Certain of these mono-sinusoidal spectra are then selected so that the diagrams which correspond to them respectively exhibit substantially analogous or complementary variations of the deviation in perceptive attribute $H-H_0$, for the series of hue samples that is used. The expression analogous or complementary variations is understood to mean values of the difference $H-H_0$ which are of the same sign or respectively positive and negative for one and the same subset of samples of hues, so as to minimize to the maximum the deviation in perceptive attribute $H-H_0$ in order to best restore the colors. It is then possible to propose a new dummy filter spectrum, in the form of a linear combination of the mono-sinusoidal spectra selected. The parameters of this combination are deduced from examining the diagrams, so as to arrive at an ordinate compensation. A new improvement of the initial color filter may then be obtained, by repeating the method of the invention on the basis of a first set of numerically generated spectra which are close to the linear combination of sinusoids that is proposed in accordance with the diagrams. The expression "spectra close to the linear combination of sinusoids that is proposed in accordance with the diagrams" is understood to mean spectra whose parametric values correspond to limited variations with respect to the parameters proposed according to the diagrams. These linear combinations of sinusoids, resulting from the linear combination of the color restitution diagrams, make it possible to minimize to the maximum the deviation in perceptive attribute $H-H_0$ so as to best restore the colors.

The invention claimed is:

1. Method of improving a color filter comprising the following steps:
   /1/ determining colorimetric coordinates of an initial color filter;
   /2/ numerically generating a first set of transmission spectra, each of the spectra of said first set having variations which correspond to one sinusoid or to an average of several sinusoids over a visible light interval;
   /3/ for each spectrum of the first set, calculating colorimetric coordinates of said spectrum;
   /4/ within the first set of numerically generated spectra, selecting a second set of spectra having colorimetric coordinates which correspond substantially to the coordinates of the initial color filter;
   /5/ for each spectrum of the second set, using a digital computer for quantitatively evaluating a dummy filter corresponding to said spectrum, a result of said evaluation characterizing a capacity of said dummy filter to restore at least one hue and being obtained by using a numerical model of color appearance to simulate a visual perception of a sample of the hue through said dummy filter; and within the second set of spectra, selecting one of the spectra which exhibits the best quantitative evaluation to constitute an improvement of the initial filter.

2. Method according to claim 1, furthermore comprising the following step:
   /6/ manufacturing an improved color filter having a transmission spectrum substantially equal to the spectrum selected in step /5/.

3. Method according to claim 1, wherein the first set of spectra is generated by varying at least one sinusoid parameter chosen from a list comprising a period, an initial phase, an amplitude and a base constant added to said sinusoids.

4. Method according to claim 1, wherein the colorimetric coordinates used in steps /1/, /3/ and /4/ are the coordinates $L^*$, $a^*$, $b^*$ of the CIELAB space.

5. Method according to claim 1, wherein step /5/ comprises the following substeps, performed for each numerically generated spectrum of the second set:
   /5-1/ obtaining, on the basis of the numerically generated spectrum and of a reflection spectrum of the hue sample, optical data relating to a simulation of an observation of said sample through a dummy filter corresponding to the numerically generated spectrum;
   /5-2/ introducing, into the numerical model of color appearance, the optical data relating to the simulation of the observation of the hue sample through the dummy filter corresponding to the numerically generated spectrum, so as to obtain, for said sample, a value of at least one visual perceptive attribute; and
   /5-3/ calculating a deviation between the perceptive attribute value obtained for the simulation of the observation of the hue sample through the dummy filter corresponding to the numerically generated spectrum and a value of said perceptive attribute for an observation of the same sample without the filter,
   said deviation forming an evaluation of the restitution of the hue of the sample by the dummy filter corresponding to the numerically generated spectrum.

6. Method according to claim 5, wherein, for each numerically generated spectrum of the second set, steps /5-1/ to /5-3/ are repeated for several samples of hues so as to obtain respective deviations of perceptive attribute for said samples of hues, and wherein the method furthermore comprises the following step:
   /5-4/ calculating a value characterizing the global restitution of the hues by the dummy filter corresponding to the numerically generated spectrum, on the basis of the set of deviations of perceptive attribute obtained respectively for the samples of hues used, said value characterizing the global restitution of the hues being used for the selection of step /5/.

7. Method according to claim 5, wherein the optical data obtained in step /5-1/ are trichromatic components relating to the simulation of the observation of the hue sample through the dummy filter corresponding to the numerically generated spectrum.

8. Method according to claim 5, wherein the visual perceptive attribute value obtained in step /5-2/ is a value of hue angle H read off from the NCS system.

9. Method according to claim 1, wherein the numerical model of color appearance used in step /5/ is the CIECAM02 model.

10. Method according to claim 1, wherein at least one of the numerically generated spectra of the first set consists of a single sinusoid, possibly added to a base constant.

11. Method according to claim 1, wherein at least one of the numerically generated spectra of the first set consists of a linear combination of several sinusoids, possibly added to a base constant.

12. Method according to claim 11, wherein the sinusoids combined together to constitute at least one of the spectra of the first set are selected beforehand so that dummy filters having respectively said sinusoids as spectra exhibit substantially analogous or complementary variations of a perceptive attribute deviation for several samples of hues, said deviation being calculated for each dummy filter and for each sample of hue between a perceptive attribute value obtained for a simulation of observation of said hue sample through the dummy filter and a value of said attribute obtained for a simulation of observation of the same sample with no filter.

13. Use of an improving method according to claim 1, to improve a tinted ophthalmic lens.

* * * * *